United States Patent [19]

Mauerer et al.

[11] Patent Number: 4,832,689
[45] Date of Patent: May 23, 1989

[54] INFUSION MEANS

[75] Inventors: Erich Mauerer, Kassel; Reiner Mengel, Niedenstein, both of Fed. Rep. of Germany

[73] Assignee: B. Braun Melsungen AG, Fed. Rep. of Germany

[21] Appl. No.: 116,489

[22] Filed: Nov. 2, 1987

[30] Foreign Application Priority Data

Nov. 6, 1986 [DE] Fed. Rep. of Germany ....... 3637771

[51] Int. Cl.$^4$ ............................................. A61M 31/00
[52] U.S. Cl. ......................................... 604/67; 604/50; 417/26
[58] Field of Search ..................... 604/67, 50, 65, 153, 604/245, 246, 250; 417/26, 36, 28, 44

[56] References Cited

U.S. PATENT DOCUMENTS

| | | | |
|---|---|---|---|
| 3,583,400 | 6/1971 | Memhardt et al. | 604/50 |
| 3,907,504 | 9/1975 | Hammond et al. | 417/36 |
| 4,207,871 | 1/1980 | Jenkins | 604/65 |
| 4,231,366 | 11/1980 | Schael | 604/67 |
| 4,319,568 | 3/1982 | Tregoning | 604/67 |
| 4,345,594 | 8/1982 | Bisera et al. | 604/67 |
| 4,389,164 | 6/1983 | Godbey et al. | 417/36 |
| 4,474,309 | 10/1984 | Solomon | 604/67 |
| 4,551,134 | 11/1985 | Slavik et al. | 604/67 |
| 4,613,325 | 9/1986 | Abrams | 604/65 |
| 4,648,872 | 3/1987 | Kamen | 604/245 |
| 4,670,007 | 6/1987 | Wheeldon et al. | 604/67 |
| 4,702,245 | 1/1988 | Takata et al. | 417/28 |
| 4,747,822 | 5/1988 | Peabody | 604/65 |

FOREIGN PATENT DOCUMENTS 2944333 5/1980 Fed. Rep. of Germany .
0862952 9/1981 U.S.S.R. ................................ 604/67

Primary Examiner—C. Fred Rosenbaum
Assistant Examiner—Denise Whelton
Attorney, Agent, or Firm—Spensley Horn Jubas & Lubitz

[57] ABSTRACT

Infusion liquid flows from a container via a hose controlled by a squeezing valve into a measuring chamber which has an existing predetermined upper filling level and a predetermined lower filling level which may be detected by a filling level detector. A hose pump conveys liquid from the measuring chamber to the patient. In order to adjust the rate of the hose pump in accordance with the provided infusion rate, the time required in case of the closed squeezing valve to pump off fluid from the upper filling level to the lower filling level is determined. Subsequently, the measuring container is refilled within a filling time, while pump is further operative or may be also stopped. The measuring chamber including the hoses connected thereto may be designed as a disposable unit.

8 Claims, 2 Drawing Sheets

INFUSION MEANS

BACKGROUND OF THE INVENTION

1. Field of the Invention

The invention relates to an apparatus for controlling the infusion rate of an infusion means.

2. Description of the Related Art

It has been known, for making infusions, i.e., for infusing a liquid into a patient, to use hose pumps in which a hose containing the liquid is continuously squeezed in order to advance therein said liquid. Accuracy of the delivery rate depends upon the accurate speed of the hose pump, on the one hand, and upon the volume accuracy of the tube, on the other hand. Above all, volume accuracy of soft PVC hoses is particularly poor. The hose of a pump used in an infusion means is typically a disposable unit which is supplied in a sterilized condition and thrown away upon its use. In the case of such hoses, volume accuracy is dictated not only by the variation of the products, but also by ageing and wear. In the case of known hose pumps in which the hose is a disposable element producible at low cost, the maximum obtainable accuracy of the feed rate is about five percent (5%). If drugs are to be infused, such a feed accuracy is frequently inadequate.

SUMMARY OF THE INVENTION

It is an object of the invention to improve the infusion accuracy of infusion means of the type having a fluid container, a hose pump for administering fluid to a patient, and a control unit for controlling the feeding rate of the hose pump.

According to one embodiment of the invention, liquid is fed by the pump from the measuring chamber, whose filling level is constantly monitored, to the patient. The actual time required to pump liquid from an upper to a lower filling level is measured and placed in relationship to a desired evacuation time $t_s$ corresponding to the desired infusion rate $FR_s$. In the case of disagreement between the actual and the desired evacuation times, the pump speed is corrected correspondingly, thus ensuring that the next evacuation cycle is performed in a time approximating or corresponding to the desired evacuation time. "Evacuation time" is meant to refer to the desired time for the pump to feed liquid in the measuring chamber from the predetermined upper filling level to the predetermined lower filling level. When the fluid level reaches the lower filling level, liquid is still contained in the measuring chamber, which is not completely emptied during the evacuation time.

The measuring time is equal to the evacuation time. This time period is followed by a filling period for filling the measuring chamber up to the predetermined upper filling level, with liquid from the liquid container. The delivery rate from the liquid container to the measuring chamber is generally substantially higher than the infusion rate and, accordingly, the filling time is much shorter than the measuring time.

At the end of the measuring time, the respective disagreement between the actual measuring time and the desired measuring time is determined to subsequently correct the pumping speed in response to the detected deviation.

The accuracy of the infusion rate is dictated substantially by the diameter accuracy of the measuring chamber and by the accuracy of the filling level detector. The infusion rate is not dependent on the accuracy of the pump and the accuracy of the volume of the pump hose. High accuracies may be obtained for the measuring container and the filling level detector so that accuracy of the infusion rate is about one to two percent. It is to be taken into account that the filling level detector may form an integral part of the assembly and need not be a disposable element thereof. Therefore, a more accurate and usually more expensive reusable filling level detector may be utilized without substantially increasing the cost per infusion. Preferably, the measuring chamber coming into contact with the liquid forms part of a disposable unit which, as a plastic article, may be produced within relatively close tolerances.

Although the liquid is supplied periodically in exactly proportioned volume amounts to the measuring chamber, a continuous infusion into a patient may be ensured if the pump remains operative during the filling time following a measuring time. During the filling time, the pump may be controlled to either operate at a newly set speed or at the speed newly calculated at the end of the measuring time.

The delivery rate of a hose pump is subject to periodic fluctuations. Therefore, each measuring time should start at a predetermined phase angle of the pump cycle. The pump should operate in the filling time subsequent to the measuring time and up to the reaching of said phase angle. In other words, the pump rotation initiated with the reaching of the upper filling level should be completed until the predetermined phase angle is reached, thus permitting to start the next measuring time again with the predetermined phase angle.

In the case of low infusion rates, it is possible to stop the pump in the filling cycle in which liquid is refilled in the measuring chamber, provided a short interruption of the liquid supply is admissible in view of the infusion.

BRIEF DESCRIPTION OF THE DRAWINGS

Some preferred embodiments of the invention will be explained herein below in more detail with reference to the drawings in which.

DESCRIPTION OF THE PREFERRED EMBODIMENTS

Figure 1:
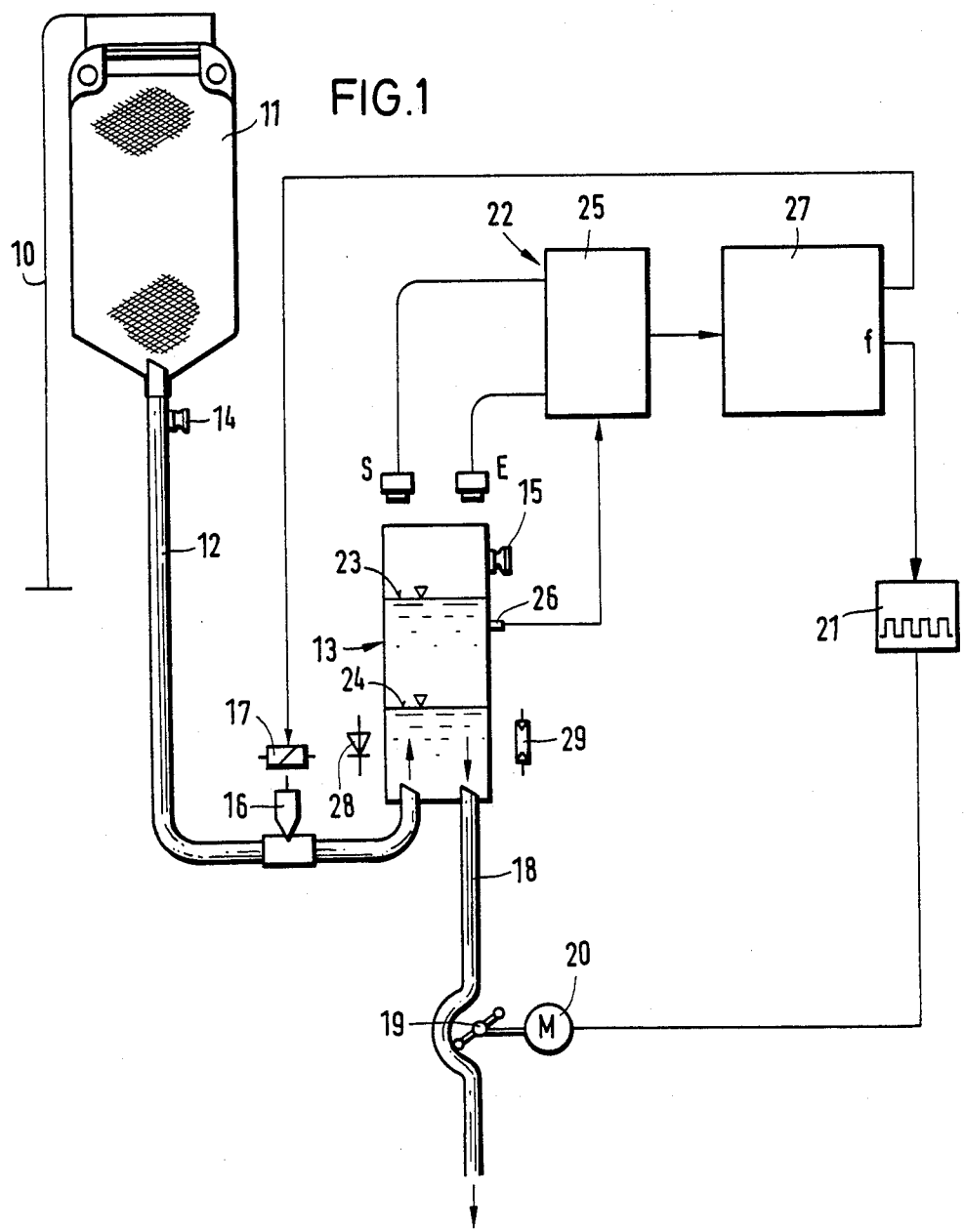
FIG. 1 is a schematic illustration of an embodiment of the infusion means.

As evident from FIG. 1, there is suspended at a holding device 10 the liquid container 11 which contains the infusion liquid, the lower end of said container 11 being connected by hose 12 to the measuring chamber 13 which is an upright rotationally symmetric hollow body. Shortly beneath liquid container 11, hose 12 extends into the bottom wall chamber 13 and includes an affixed air filter 14. Another air filter 15 is provided near the upper end of the measuring chamber 13. The height position of the liquid container 11 is such as to ensure that its lower end is situated above the level of the upper end of the measuring chamber 13, thus allowing liquid to flow from the liquid container 11 into the measuring chamber 13. A squeezing valve 16 operated by a magnet 17 and adapted to lock hose 12 is provided at one point of the hose 12.

From the lower end of the measuring chamber 13, another hose 18 extends to the patient. A hose pump 19 of the peristaltic or roller type, which includes at least two rotating elements, is provided to continuously squeeze a section of hose 18. Hose pump 19 is driven by motor 20.

In the instant embodiment, motor 22 is a stepping motor provided with pulses by pulse generator 21. The rotating speed of hose pump 19 is proportional to the pulse frequency supplied by the pulse generator 21.

The filling level detector 22 detecting the filling level of measuring chamber 13 supplies a first signal if a specific upper filling level 23 is reached. A second signal is given upon reaching a specific lower filling level 24. The filling level detector 22 is operated, in the instant embodiment, by ultrasonic measurement. An ultrasonic measuring device 25 energizes an ultrasonic transmitter S by which, from above, ultrasonic waves are sent into measuring chamber 13. The ultrasonic waves are reflected by the respective fluid level and supplied to the receiver E. From the delay of the ultrasonic signals, measuring means 25 determines the height of the respective fluid level. There are ultrasonic distance meters which are operating with a resolution of ±0.025 mm and thus are able to detect very precisely the two fluid levels 23 and 24. To eliminate probable influences of temperature (e.g., temperature dependency of sound velocity), a temperature sensor 26 affixed to the measuring chamber 13 supplies a temperature-dependent signal to the measuring means 25 by which compensation of temperature may be ensured.

A signal corresponding to the level height in the measuring chamber is supplied from the measuring means 25 of the control unit 27 adapted to control frequency f of the frequency generator 21 and the magnetic valve 16, 17.

As obvious from FIG. 1, the measuring chamber 13 includes a photoelectric safety means comprising a light-emitting diode 28 and a light receiver 29. The safety means 28, 29 forms a light barrier to detect whether the fluid level has lowered to a specific lower level beneath the fluid level 24. If so, hose pump 19 is turned off by emergency in order to prevent air from being pumped into the patient's body.

If the assembly shown in FIG. 1 is in operation, squeezing valve 16 is opened, thus allowing fluid to flow from container 11 into measuring chamber 13. If the upper filling level 23 is reached, the squeezing valve 16 is closed by the control device 27. Hose pump 19 begins to operate to pump fluid from the measuring chamber 13 through hose 18 to the patient.

Figure 2:
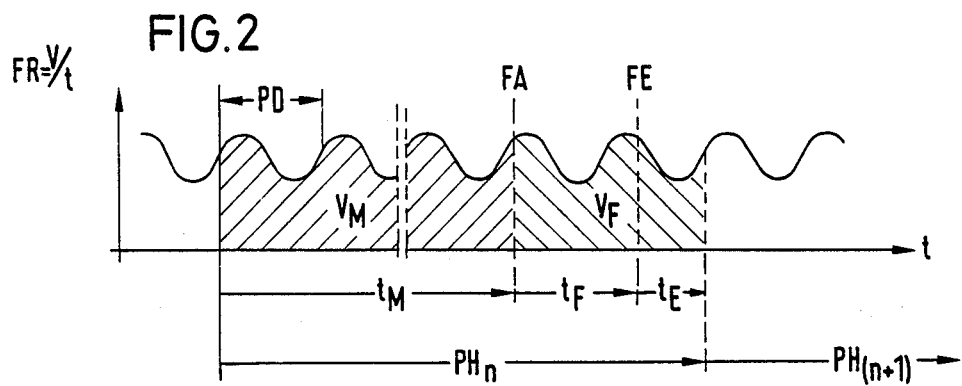
FIG. 2 is a time diagram of the pump feeding rate.

FIG. 2 shows the feeding rate FR of the hose pump, said feeding rate being defined as delivery volume V per time unit t. It is recognizable that the delivery rate periodically changes. However, the period time PD always corresponds to one rotation of the hose pump. The pump volume $V_M$ during the measuring time $t_M$ corresponds to the integral of the feeding rate FR in the measuring time $t_M$. This integral is illustrated in FIG. 2 by the surface hatched obliquely to the right top. The measuring time $t_M$ is terminated when the lower filling level 24 is reached, and the filling time $t_F$ then starts immediately at moment FA (beginning of filling). The filling time is a factor resulting from the duration of the required filling operation and is not predeterminable. It ends at moment FE (filling end), when the upper filling level 23 is reached. The filling time $t_F$ is followed additionally by a supplementaion time $t_E$, during which the hose pump goes on operating to the end of the initiated rotation, allowing the next measuring period to start with a defined phase position of the hose pump.

The measuring time $t_M$, which is required by hose pump 19 to lower the content of the measuring chamber 13 from the upper fluid level 23 to the lower fluid level 24, is measured in control unit 27. Additionally, the pumping speed $v_{(n+1)}$ to be adjusted for the next phase (sum of times $t_M$, $t_F$ and $t_E$) is calculated according to the formula $$v_{(n+1)} = (T_{Mn}t_S) \cdot V_n \tag{1}$$

where $v_n$ is the pump velocity in the just terminated n-th phase $PH_n$, $v_{(n+1)}$ is the pumping velocity to be set for the next phase $PH_{(n+1)}$, $T_{Mn}$ is the duration of the measuring time $T_M$ in the n-th phase and $t_S$ represents the desired time in which the measuring container should be emptied from filling level 23 to filling level 24.

Concerning the desired time, the formula $$t_S = MV/FR_S \tag{2}$$

is applicable, where MV means the measuring volume of the measuring chamber 13 between filling levels 23 and 24 while $FR_S$ is the desired feeding rate or the desired infusion rate respectively.

In the case of the disclosed embodiment, the pump velocity v is proportional to the frequency f of the pulses supplied to the stepping motor 20. Therefore, it is possible to replace the above equation by:

$$f_{(n+1)} = (T_{Mn}/t_S)f_n \tag{3}$$

where $f_n$ is the pulse frequency in the respective phase $PH_n$ and $f_{n+1}$ is the frequency to be set for the next phase $PH_{(n+1)}$.

It is possible to replace the stepping motor 20 with a DC motor or another motor type having an adjustable speed. In such a case, a position monitor is connected downstream of the motor to measure the rotary position of the pump shaft and to signal the position to control unit 27. Thus, the pump velocity is readjusted from phase to phase by the control unit 27 in the same way as shown in the embodiment illustrated in FIG. 1.

Assuming that the adjusted feeding rate $FR_S$ is 600 ml/h (milliliters per hour), while the volume of the measuring chamber 13 between filling levels 23 and 24 is 15 ml (milliliters), the delivery time for pumping off the measuring volume MV of 15 ml is 90 seconds. The hose pump will require, e.g., 34 revolutions to this effect.

As a rule, the pumping time $t_F$ required to refill the measuring volume will be about 5 seconds. In other words, the hose pump will perform 1.89 revolutions while the measuring volume is refilled and in said time, 0.88 ml of liquid will be pumped.

It is possible for hose 12 to comprise another pump between fluid container 11 and squeezing valve 16 in order to shorten the filling time of the measuring chamber 13 or to exclude a higher mounting of the fluid container 11.

Figure 3:
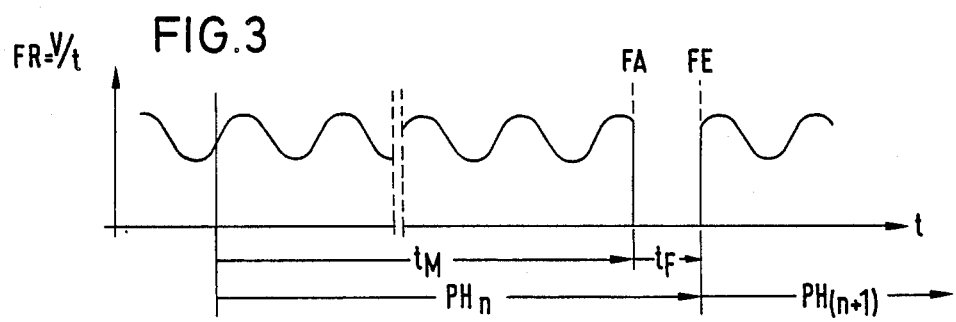
FIG. 3 is a time diagram similar to that of FIG. 2 in the case of another performance of the pump.

FIG. 3 shows another operation mode of the pump in the case of low feeding quantities, when the measuring time $t_M$ is very long while the pump is arrested during the filling time $t_F$. The filling time is dictated by the residual volume of the liquid container 11 and is measured accordingly. At the moment FE, the pump again operates at the same phase angle at which it stopped before. Therefore, a supplementation time $t_E$ is not required. During this operation mode, the desired time in which the measuring volume shall be pumped off the measuring chamber 13 is calculated as follows:

$$t_S = (MV/FR_S) - t_F \tag{2a}$$

By this means, it is ensured that the amount of liquid administered to the patient during the measuring time $t_M$ is sufficient for the sum of times $t_M + t_F$ in order to reach the desired feeding rate $FR_S$.

Figure 4:
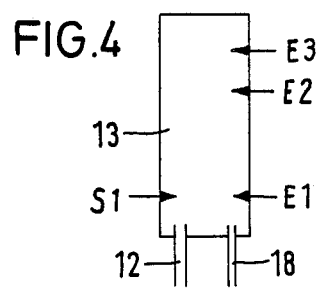
FIG. 4 is a modified embodiment of the measuring chamber with integrated filling level detector.

FIG. 4 shows another embodiment of a filling level detector in which a plurality of electrodes S1, E1, E2, E3 are accommodated in the wall of measuring chamber 13. Each electrode comes into contact with liquid when it has reached the height of the respective electrode. A transmitting electrode S1 applies a voltage potential to the liquid. If said voltage potential is received by one of the receiving electrodes E1 to E3, one may be sure that it is wetted with liquid. The lower receiving electrode E1 is positioned as high as the lower liquid level 24, while the upper receiving electrode E3 is as high as the upper liquid level 23. An auxiliary electrode E2 disposed beneath the upper receiving electrode E3 is responsible or the partial closure of the squeezing valve 16 when liquid has reached the level of auxiliary electrode E2. Thus, in the final filling phase of the measuring chamber 13, liquid rises more slowly to avoid overflooding of electrode E3.

Figure 5:
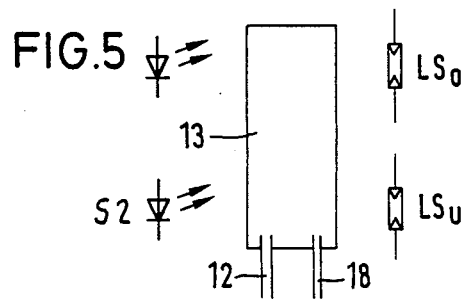
FIG. 5 is another modified embodiment of the measuring chamber with external filling level detector.

FIG. 5 shows another embodiment of the filling level detector comprising two light barriers $LS_U$ and $LS_O$ whose light beams pass through the transparent walls of the measuring chamber 13. The light beams of the light barriers $LS_U$ and $LS_O$ are exactly focused. It is also possible in such a case to predetect the upper filling level by an auxiliary light barrier arranged beneath the upper light barrier $LS_O$.

Hoses 12 and 18 as well as measuring chamber 13 and the liquid container 11 form a disposable unit delivered as a sterilized package adapted to be mounted in the device and to be thrown away upon termination of the infusion.

What is claimed is:

1. An infusion means comprising:
    a fluid container;
    a hose pump for administering fluid to a patient at a controlled rate;
    a measuring chamber provided between the fluid container and the hose pump;
    filling level detection means for detecting a lower level of fluid in the measuring chamber and an upper level of fluid in the measuring chamber;
    control means for releasing fluid from the fluid container to the measuring chamber when fluid in the measuring chamber reaches the lower level and for stopping the release of fluid from the fluid container to the measuring chamber when fluid in the measuring chamber reaches the upper level;
    measuring means for measuring a first time period between the time that fluid in the measuring chamber reaches the upper level and the time that fluid in the measuring chamber reaches the lower level,
    calculating means for calculating a quotient equal to the first time period divided by a second predetermined time period,
    adjustment means for adjusting the pump speed after lapse of the first time period by an amount proportional to the calculated quotient.

2. An infusion means as defined in claim 1 wherein the measuring chamber is a disposable unit.

3. An infusion means as defined in claim 1 wherein a third time period is defined by the time that fluid in the measuring chamber reaches the lower level and the time that fluid in the measuring chamber reaches the upper level, the infusion means further comprising:
    means for operating the pump at a substantially constant speed during the third time period, the speed of the pump during the third time period being substantially equal to the speed of the pump during the preceding first time period.

4. An infusion means as defined in claim 1 wherein a third time period is defined by the time that fluid in the measuring chamber reaches the lower level and the time that fluid in the measuring chamber reaches the upper level, the infusion means further comprising:
    means for operating the pump at a substantially constant speed during the third time period, the speed of the pump during the third time period being substantially equal to the adjusted speed of the pump after lapse of the preceding first time period.

5. An infusion means as defined in claim 1 wherein a third time period is defined by the time that fluid in the measuring chamber reaches the lower level and the time that fluid in the measuring chamber reaches the upper level, the infusion means further comprising:
    means for positioning the pump at a predetermined phase angle at the start of the first time period, and
    means for returning the pump to the predetermined phase angle subsequent to the first time period and the third time period.

6. An infusion means as defined in claim 1 wherein a third time period is defined by the time that fluid in the measuring chamber reaches the lower level and the time that fluid in the measuring chamber reaches the upper level, the infusion means further comprising means for arresting the pump during the third time period.

7. An infusion means as defined in claim 1 further comprising:
    a line extending from the fluid container to the measuring chamber, and
    a squeezing valve provided in the line extending from the fluid container to the measuring chamber, wherein the control means further includes means for operating the squeezing valve.

8. In an infusion means including a fluid container, a hose pump for administering fluid to a patient at a controlled rate, and a measuring chamber provided between the fluid container and the hose pump, an infusion process comprising the steps of:
    detecting a lower level of fluid in the measuring chamber,
    detecting an upper level of fluid in the measuring chamber,
    releasing fluid from the fluid container to the measuring chamber when fluid in the measuring chamber reaches the lower level,
    stopping the release of fluid from the fluid container to the measuring chamber when fluid in the measuring chamber reaches the upper level,
    measuring a first time period between the time that fluid in the measuring chamber reaches the upper level and the time that fluid in the measuring chamber reaches the lower level,
    calculating a quotient equal to the first time period divided by a second, predetermined time period, and
    adjusting the pump speed after lapse of the first time period by an amount proportional to the calculated quotient.

* * * * *